(12) United States Patent
Goldbecher

(10) Patent No.: US 10,507,078 B2
(45) Date of Patent: Dec. 17, 2019

(54) TOOL FOR TREATMENT OF INTERDENTAL SURFACES

(71) Applicant: Heiko Goldbecher, Halle (DE)

(72) Inventor: Heiko Goldbecher, Halle (DE)

(73) Assignee: INTENSIV SA (CH)

( * ) Notice: Subject to any disclaimer, the term of this patent is extended or adjusted under 35 U.S.C. 154(b) by 2 days.

(21) Appl. No.: 15/383,352

(22) Filed: Dec. 19, 2016

(65) Prior Publication Data

US 2017/0172705 A1    Jun. 22, 2017

(30) Foreign Application Priority Data

Dec. 22, 2015 (EP) .................................... 15201863

(51) Int. Cl.
*A61C 3/06* (2006.01)
*A61C 15/00* (2006.01)

(52) U.S. Cl.
CPC ................ *A61C 3/06* (2013.01); *A61C 15/00* (2013.01)

(58) Field of Classification Search
CPC .................................. A61C 3/06; A61C 15/00
See application file for complete search history.

(56) References Cited

U.S. PATENT DOCUMENTS

| | | | | |
|---|---|---|---|---|
| 3,779,256 A | * | 12/1973 | Maloney | A61C 15/02 132/329 |
| 4,187,082 A | * | 2/1980 | Guerra | A61C 3/06 433/229 |
| 4,271,854 A | * | 6/1981 | Bengtsson | A61C 15/02 132/329 |
| 4,563,152 A | * | 1/1986 | McClure | A61C 5/85 432/142 |
| 4,592,729 A | * | 6/1986 | Bilciurescu | A61C 3/06 433/142 |
| 5,476,381 A | * | 12/1995 | Dragan | A61C 3/06 30/169 |
| 5,836,810 A | * | 11/1998 | Asum | A61C 3/06 433/142 |
| 7,322,822 B2 | * | 1/2008 | Navarro | A61C 3/06 433/125 |
| 7,758,343 B1 | * | 7/2010 | Navarro | A61C 3/06 433/125 |
| 8,915,734 B2 | * | 12/2014 | Deleon | A61C 15/00 433/141 |
| 9,237,938 B2 | * | 1/2016 | Van Putten | A61C 3/06 |
| 2002/0119421 A1 | * | 8/2002 | Gratz | A61C 3/06 433/142 |
| 2004/0163664 A1 | * | 8/2004 | Husted | A61C 3/06 132/321 |

(Continued)

FOREIGN PATENT DOCUMENTS

DE    10 2011 014992 A1    9/2012

OTHER PUBLICATIONS

European Search Report dated May 23, 2016 issued in corresponding European application No. 15 20 1863.

*Primary Examiner* — Cris L. Rodriguez
*Assistant Examiner* — Hao D Mai
(74) *Attorney, Agent, or Firm* — Ostrolenk Faber LLP

(57) ABSTRACT

The tool for treatment of interdental surfaces includes a strip (10) having an abrasive field (12) on at least one of its longitudinal sides (11). The field is situated at a distance (A) from the apical edge (11a) of the longitudinal side, the longitudinal side being blank between the apical edge and the field.

16 Claims, 3 Drawing Sheets

(56) References Cited

U.S. PATENT DOCUMENTS

| | | | |
|---|---|---|---|
| 2005/0058963 A1* | 3/2005 | Stockstill | A61C 3/06 433/166 |
| 2005/0244786 A1 | 11/2005 | Freedman | |
| 2005/0271999 A1* | 12/2005 | Fishburne, Jr. | A61C 3/03 433/39 |
| 2007/0148613 A1* | 6/2007 | Stoll | A61C 5/85 433/39 |
| 2011/0081830 A1 | 4/2011 | Pollasky | |
| 2011/0200963 A1* | 8/2011 | Allen | A61C 3/06 433/142 |
| 2012/0244494 A1 | 9/2012 | Navarro | |
| 2014/0220507 A1 | 8/2014 | Van Putten | |

* cited by examiner

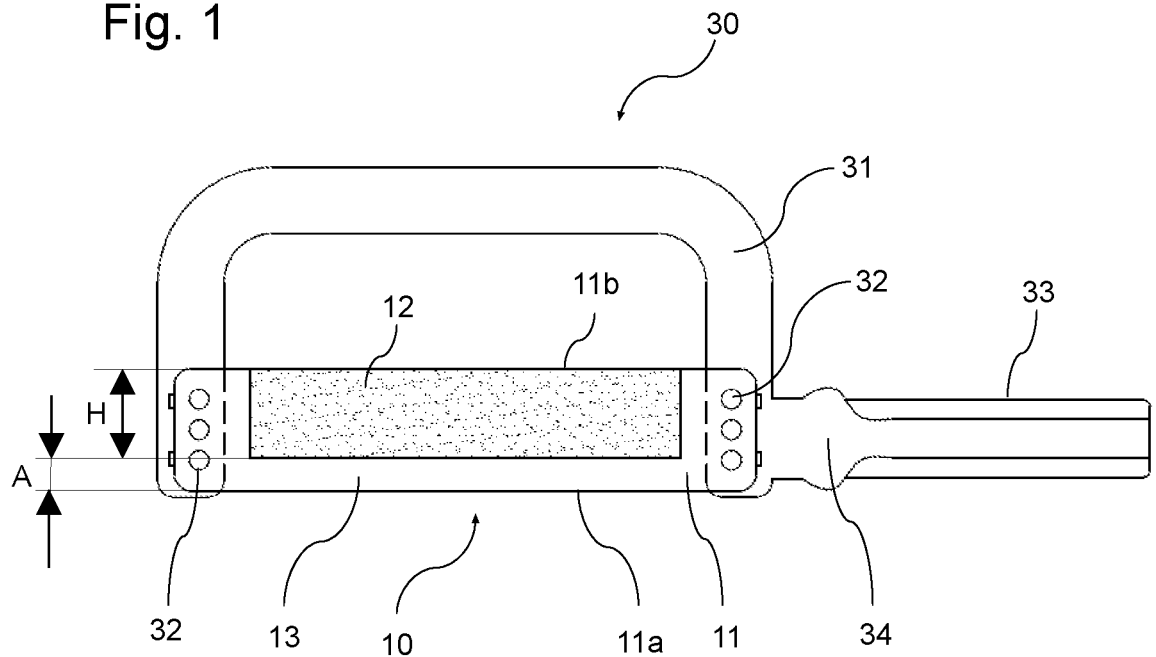
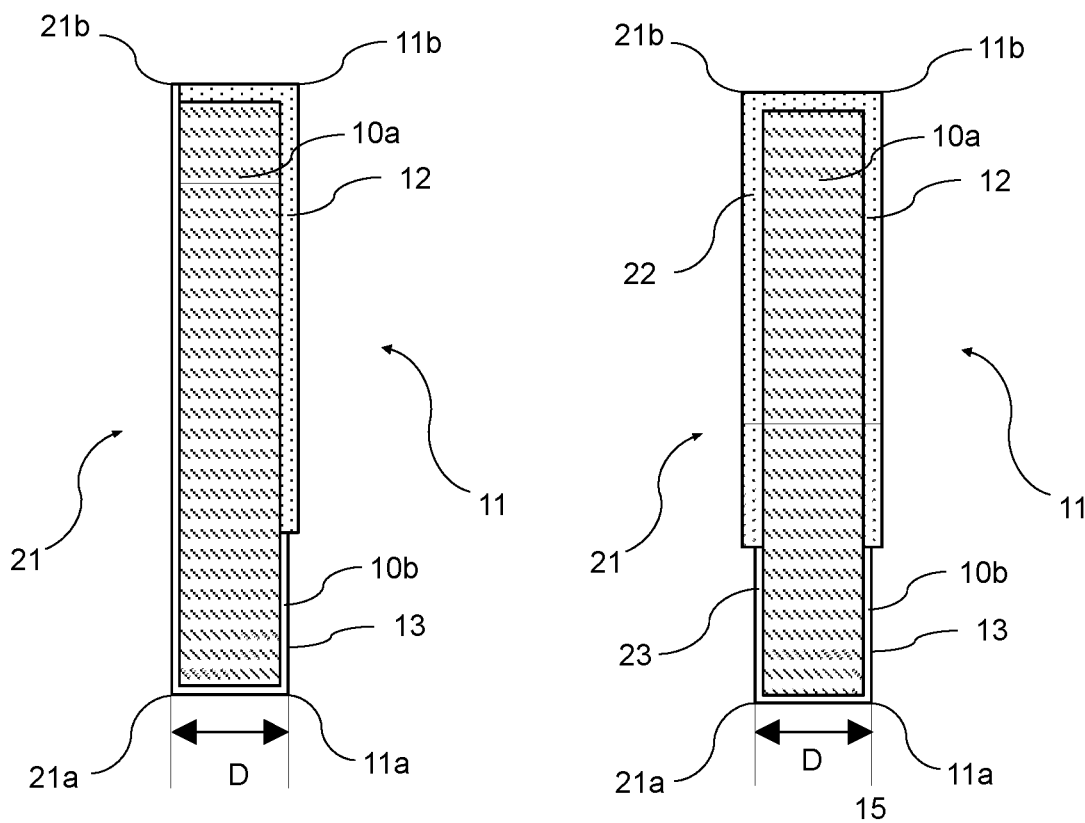

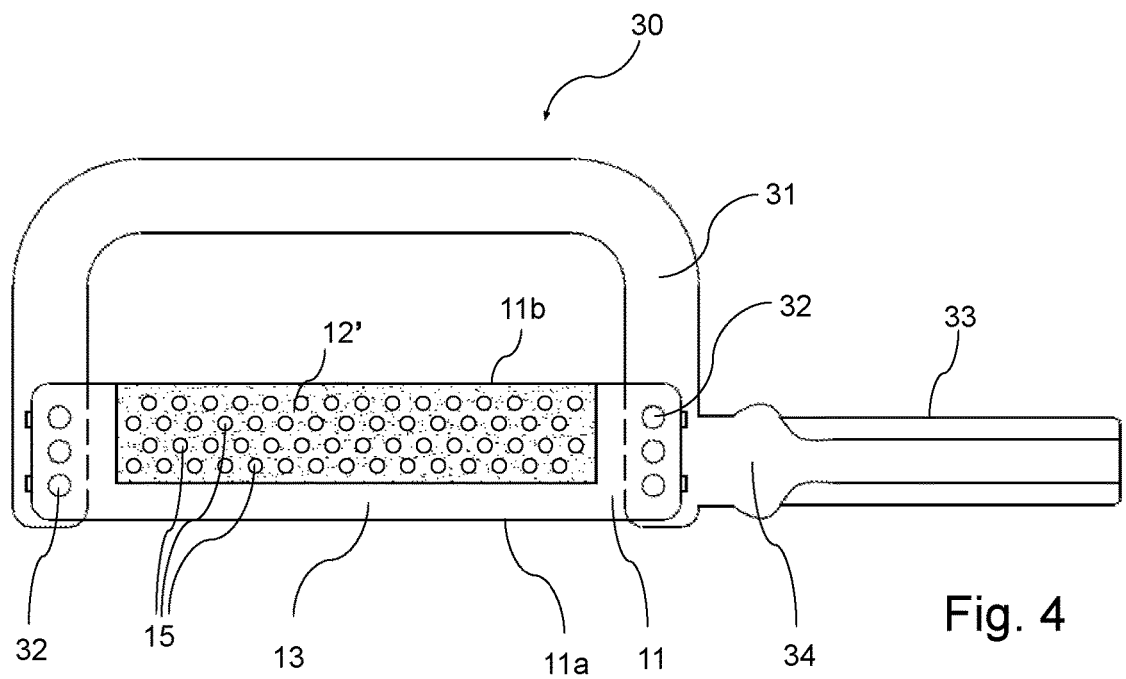
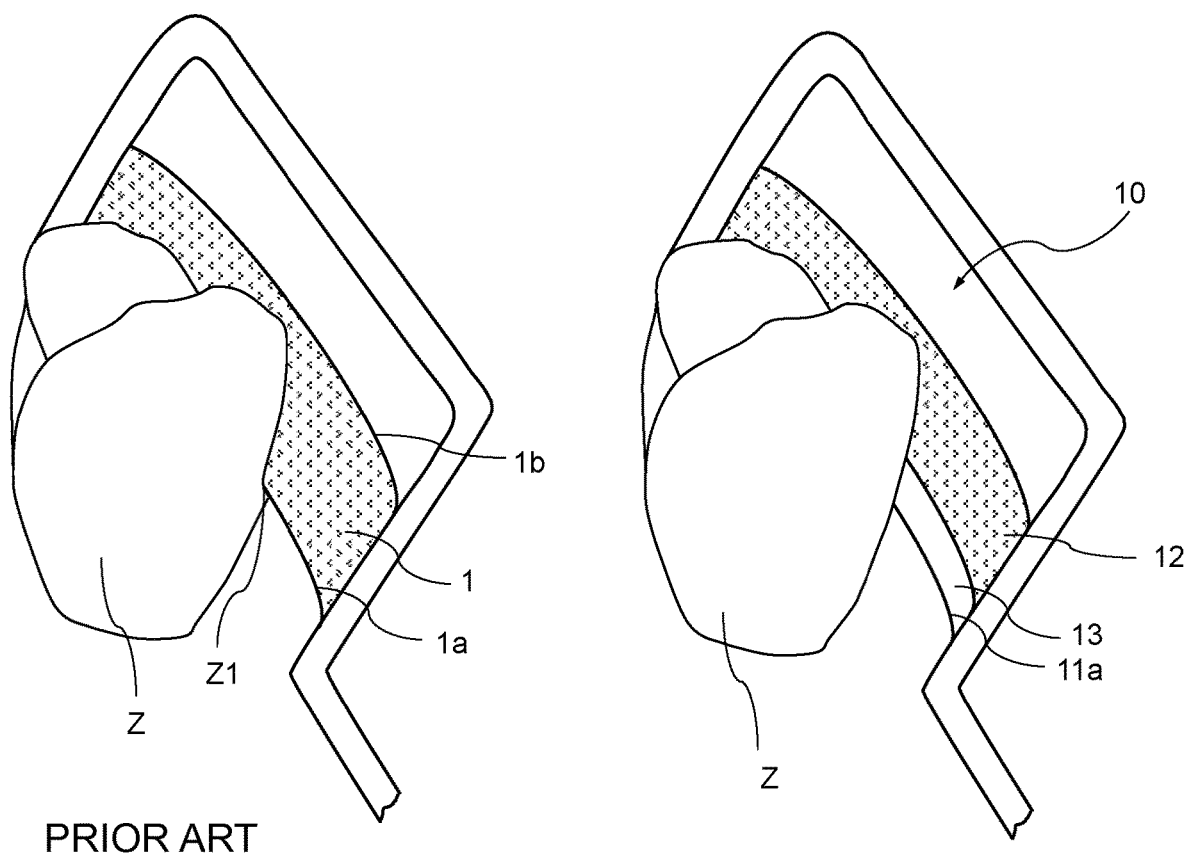
PRIOR ART
Fig. 5
Fig. 6

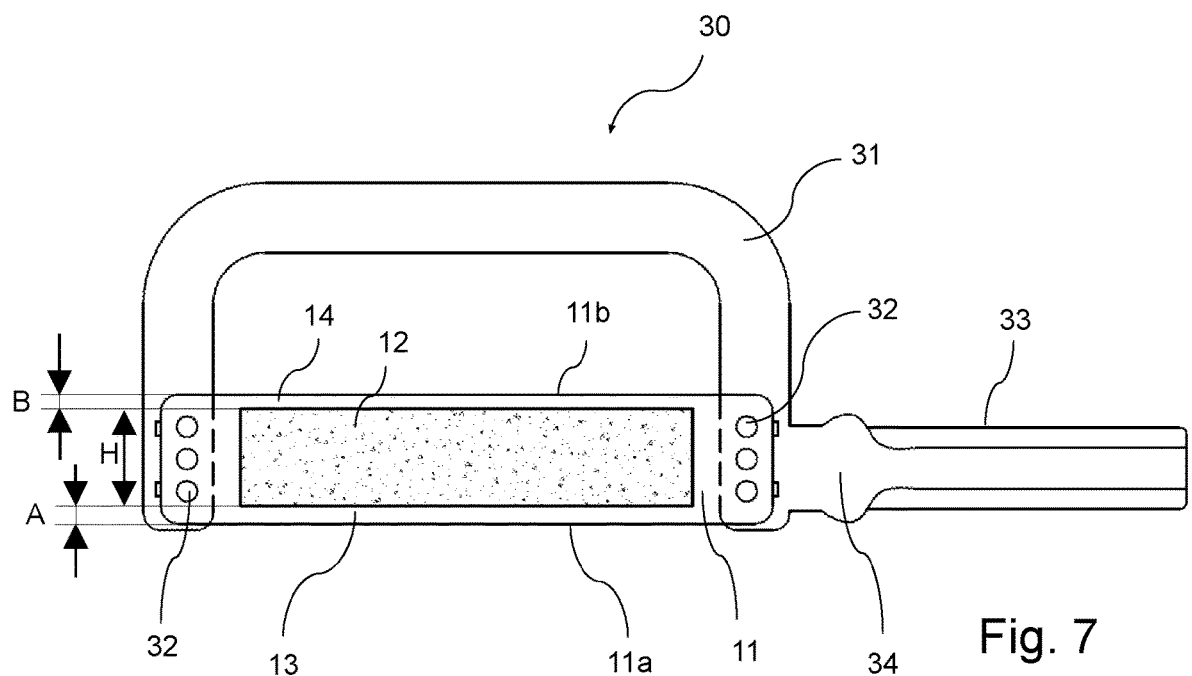
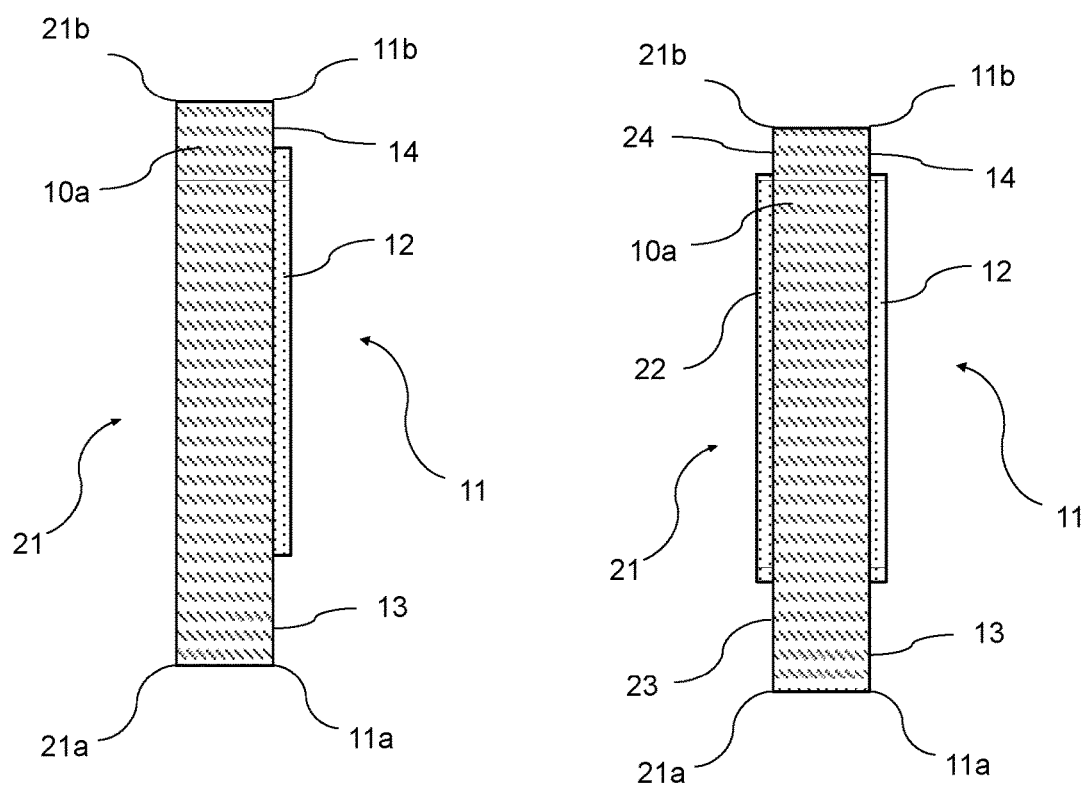

TOOL FOR TREATMENT OF INTERDENTAL SURFACES

BACKGROUND

The invention relates to a tool for treatment of interdental surfaces, which comprises a strip with an abrasive field.

Tools of this kind have an abrasive action and are used particularly in the field of orthodontics, e.g. to remove the dental enamel approximately, in order to reduce the size of the teeth and, in the case of a number of teeth, to make room for the movement of the teeth during the orthodontic treatment.

The tools used until now comprise a strip that is completely covered with abrasive particles both vertically and horizontally. On one hand, this makes it difficult to insert the strip between the teeth during the clinical treatment, particularly in the case of crowded teeth. On the other hand, even slight canting of the strip at its apical end may cause the formation of undesirable steps in the tooth surface.

SUMMARY

It is an object of the present invention to improve the tool in such a manner as to simplify its handling and to avoid the formation of steps at the apical end of the strip during the treatment of an interdental surface.

This object is achieved by a tool, wherein the abrasive field is situated at a distance from an apical edge and wherein the longitudinal side is blank between the apical edge and the field. Thereby, the introduction of the strip into the interdental space is facilitated and the formation of steps is avoided.

BRIEF DESCRIPTION OF DRAWINGS

Further specific constructive features and their advantages will become apparent from the following description and from the drawing of exemplary embodiments, where FIG. 1 shows a first exemplary embodiment of a tool according to the invention in a lateral view, FIG. 2 shows a first variant of a strip for a tool according to FIG. 1 in cross-section, FIG. 3 shows a second variant of a strip for a tool according to FIG. 1 in cross-section, FIG. 4 shows a second exemplary embodiment of a tool according to the invention in a lateral view, FIG. 5 shows the impact of a tool of the prior art on a tooth, FIG. 6 shows the impact of the tool according to the invention on a tooth, FIG. 7 shows a third embodiment of a tool according to the invention in a side view, FIG. 8 shows a first variant of a strip for a tool according to FIG. 7 in a sectioned view, and FIG. 9 shows a second variant of a strip for a tool according to FIG. 7 in a sectioned view.

DETAILED DESCRIPTION

FIG. 1 shows a first exemplary embodiment of a tool for the treatment of interdental surfaces, which comprises a strip 10 and a retaining part 30.

The strip 10 has two longitudinal sides which will be referred to as front side 11 and rear side 21 hereafter. The front side 11 is located between an apical edge 11a and a coronal edge 11b. When the strip 10 is introduced between the teeth, the apical edge 11a is nearer to the tooth base than the coronal edge 11b. Correspondingly, the rear side 21 is located between an apical edge 21a and a coronal edge 21b; see the cross-sections in FIGS. 2 and 3. In these two Figures, the proportions with regard to the thicknesses of the different layers 10a, 10b, 12, 22 are not true to scale. Generally, the strip 10 has a cross section, which is substantially rectangular.

The respective apical edges 11a, 21a are substantially straight here. In the present example, as seen in the lateral view of FIG. 1, the strip 10 has a substantially rectangular shape.

In the example according to FIGS. 1 and 2, the front side 11 has a strip-shaped field 12 that is provided with an abrasive material, e.g. with diamond grains, and is situated at a distance from the apical edge 11a. The abrasive material comprises grains of a size typically in the range of 1-200 micrometers. For example, the grain size is equal to at least 5 micrometers, preferably at least 8 micrometers, and/or at most 100 micrometers, preferably 90 micrometers.

Between the field 12 and the apical edge 11a, a field 13 results which is blank, i.e. free from abrasive material. In FIG. 1, the distance between the field 12 and the apical edge 11a is denoted by A. This distance A is adapted to the intended application. It is typically equal to at least 0.2 mm, preferably at least 0.5 mm, and/or at most 2 mm, preferably at most 1.5 mm.

H denotes the height of the field 12. It is typically equal to at least 2 mm, preferably at least 2.5 mm, and/or at most 5 mm, preferably at most 4 mm. Generally, the height H is to be chosen greater than the distance A.

D denotes the thickness of the strip 10, measured in the area of the blank field 13. It is typically equal to at least 0.03 mm, preferably at least 0.05 mm, and/or at most 0.2 mm, preferably at most 0.3 mm.

There may be provided a set of tools 10, 30 having different values for at least one of the following parameters: A, D, H, grain size of the abrasive material, geometrical design of the strip 10. Said design may e.g. vary in that the strip is continuous or perforated (cf. FIGS. 1 and 4) and/or in that apical edge 11a is straight, serrated, or otherwise shaped.

In the example of FIG. 2, only the front side 11 is provided with an abrasive field 12. FIG. 3 shows a variant of the strip where the rear side 21 also has a field 22, which is provided with the abrasive material and which is spaced the apart from apical edge 21a so that a blank field 23 results therebetween. In the example of FIG. 3, the distance of the field 22 from the apical edge 21a is equal to the distance A of the field 12. These distances may be different, however.

As another variant, a mirror-symmetrical configuration of the variant of FIG. 2 may be contemplated where only the rear side 21 is provided with an abrasive field 22 that is spaced apart from the apical edge 21a whereas the front side 11 is blank.

In the present example, the strip 10 is composed of multiple layers. It has a first layer 10a that serves as the support and is e.g. made of metal or of a synthetic material (plastics) and to which the abrasive material, e.g. in the form of diamond particles, is applied to form at least one abrasive field 12, 22. The upper area between the coronal edges 11b and 21b may be covered with abrasive material or free of the latter. At least at the bottom, in the area of the blank field 13, 23, a second layer 10b is provided which has a particularly smooth surface. The layer 10b may also be applied to other areas of the strip, e.g. in the variant according to FIG. 2 to the entire rear side 21 and/or, particularly when the layer 10b is thinner that the grain size of the abrasive material, to the field 12, 22. By a suitable choice of the layer 10*b*, a surface is achieved in the blank field 13, 23 at the bottom of the strip which provides a reduced friction between the tooth and strip 10 during its insertion into the interdental space. Accordingly, layer 10*b* has a smaller friction coefficient than the layer 10*a*. For example, the layer 10*b* is made of titanium nitride or of a carbon layer, more particularly an amorphous carbon layer (so-called "diamond-like carbon", DLC). The thickness of the layer 10*b* is typically in the range of 0.5-2 micrometers.

Alternatively to the sequence of the layers according to FIGS. 2 and 3 it is also possible to first apply the second layer 10*b* to the first layer 10*a* and only then to apply the abrasive material 12, 22. Generally, the second layer 10*b* completely surrounds the first layer 10*a* so that the latter forms an inner layer.

In a further variant it is possible to omit the second layer 10*b* and to treat the surface of the first layer 10*a* so as to make it smoother. For example, this surface may be polished, more particularly electropolished.

During the manufacture of the strip 10, after producing the layer 10*a* and, as the case may be, the layer 10*b*, the portion of the strip that extends from the field 13 via the edges 11*a*, 21*a* the field 23 is covered with a cover layer. If one of the longitudinal sides 11 or 21 is to remain free of an abrasive field 12, 22, the entire longitudinal side is covered. Then follows a galvanic coating process during which the abrasive particles, e.g. diamond particles, are applied to the uncovered portion of the strip, thereby forming the field 12 and/or 22. Then the cover layer is removed. As mentioned above, the layer 10*b* may be applied before or after applying the abrasive material, or else omitted.

The retaining part 30 shown in FIG. 1 has a bow 31 to which the strip 10 is fixed at its ends, e.g. by soldering at points 32 or by other joining techniques. Laterally adjacent to bow 31 and on the height of the strip 10, a handle member 33 is attached which is intended here to be inserted into an appliance for moving the tool 10, 30 back and forth in the direction of extension of the strip 10 by a defined stroke. Said appliance may e.g. be an anglepiece designed to selectively produce a rotating or a linear movement.

If multiple tools 10, 30 with different designs of the strip 10 are provided, each tool 10, 30 may have a unique mark for a better distinction. For example, there may be an area e.g. on bow 31 or an area 34 near handle member 33 that is provided with a distinct color assigned e.g. to a particular grain size of the abrasive material and/or to a particular value for D.

In FIGS. 1 to 3, the abrasive field 12, 22 is provided with a continuous layer of abrasive material. It is also possible to provide gaps within an abrasive field 12, 22 and/or in another part of the strip 10. FIG. 4 shows a variant where the field 12' is perforated. To this end, it is provided with holes 15 that are e.g. arranged according to a grid. Apart from that, the design of the tool is the same as in the example of FIG. 1. Thus, in the variant according to FIG. 4, there is a blank field 13 between the field 12' and the apical edge 11*a*. Alternatively or additionally, other parts of the strip may be perforated, e.g. the field 13.

FIG. 7 shows an example, in which the abrasive field 12 is distanced away from the coronal edge 11*b*. Thereby, a blank field 14 is provided which is arranged between the abrasive field 12 and the coronal edge 11*b*. The distance B between the coronal edge 11*b* and the abrasive field 12 may be equal, smaller or greater than the distance A between the apical edge 11*a* and the abrasive field 12. The distance B is chosen to be smaller than the height H of the abrasive field 12 and is typically at least 0.2 mm, preferably at least 0.5 mm and/or at most 2 mm, preferably at most 1.5 mm. Provision of the blank field 14 makes it for the dentist easier to maintain the anatomical shape of a tooth when using the strip. In particular, the risk is reduced that the sides of the teeth are flattened such that an unwanted enlarged contact area is produced.

The example shown in FIG. 7 may have the similar variants as the example of FIG. 1:

The strip may have an abrasive field 12 only on one side, e.g. side 11 as shown in FIG. 8, or it may have abrasive fields 12, 22 on both sides 11 and 21 as shown in FIG. 9. In the latter case, there may be provided a blank field 24 between the coronal edge 21*b* and the abrasive field 22 which is similar to the blank field 14.

The non-abrasive portions of the strip such as the blank fields 13, 14, the side 21 as in FIG. 8 and the blank fields 23, 24 as in FIG. 9, may have a smooth surface, which is produced e. g. by polishing and/or by providing an additional layer similar to the layer 10*b* shown in FIGS. 2 and 3.

The strip may be perforated as in the example shown in FIG. 4.

The tool 10, 30 according to FIGS. 1 to 4 and 7 to 9 is designed for being used with an appliance that produces the desired movement of the tool, e.g. a reciprocating movement of +0.9 mm resp. −0.9 mm relative to the zero position and with 20,000 movements per minute.

It is also possible to design the tool for a purely manual application. In this variant, only the bow 31 may be provided and the handle member 33 may be omitted. In a particularly simple embodiment, no retaining part 30 is provided so that the tool merely comprises the strip 10. In this variant, in order to facilitate its handling, the ends of the strip 10 may be enlarged so as to form handle portions.

The tool described here is applicable in the treatment of interdental surfaces, more particularly for approximal enamel reduction in orthodontics. During the reciprocating movement of the tool, the enamel is abraded. This serves for reducing the size of the teeth, typically by less than 0.5 mm per tooth, and in the case of several teeth, for making room for the movement of the teeth during the orthodontic treatment. Besides enamel reduction, the tool is also applicable for finishing and polishing.

The tool offers the advantage, among others, that its introduction into the interdental space is facilitated and an undesirable formation of steps is avoided. This becomes apparent from the comparison of the two FIGS. 5 and 6 where Z denotes a tooth. The adjacent tooth is not illustrated in the Figures. In the situation according to FIG. 5, a tool of the prior art is used with a strip 1 whose front side is provided with abrasive material from the coronal edge 1*b* down to and including the apical edge 1*a*. During the insertion of the tool, the apical edge 1*a* enters into contact with the teeth first. If the space is small, the insertion itself will already be difficult due to the presence of abrasive material on the edge 1*a*. When the strip 1 is inserted into the space, even slight canting may cause the abrasive action of the strip 1 in the area of the apical edge 1*a* to create an unwanted step Z1 in the tooth. FIG. 6 shows the situation when the tool 10, 30 described herein is used. The strip 10 has a blank field 13 in the area of its apical edge 11*a*. This field has better gliding properties than the field 12 so that an easy introduction is ensured even in the presence of crowded teeth. The field 13 is free of abrasive material so that any formation of steps in tooth Z is avoided even when the strip is canted. In FIG. 6, the strip 10 is shown during its usage. Since it is not completely rigid, but has some flexibility, it will be curved due to the forces acting from the tooth surface to be treated. In the unloaded state as shown in the other FIGS. 1 to 4 and 7 to 9, the strip 10 has straight apical and coronal edges 11a, 11b.

From the foregoing description, numerous modifications will be apparent to one skilled in the art without departing from the scope of the invention, which is defined by the claims.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A tool for treatment of interdental surfaces,
    said tool having a tool longitudinal axis and a first and a second lateral end along said tool longitudinal axis;
    a handle configured for coupling said tool to an appliance capable of applying a linear movement to said tool;
    a strip comprising a support and including at least one longitudinal side;
    said strip extending from a first lateral end of said tool along said tool longitudinal axis to a second lateral end of said tool;
    said at least one longitudinal side of said strip comprising an apical edge extending along a first portion of said longitudinal axis and a coronal edge extending along a second portion of said longitudinal axis, both said apical edge and said coronal edge being straight;
    an abrasive field on said at least one longitudinal side of said strip is provided with abrasive particles which are arranged on said support, said support being flat so that it is free of geometrical protrusions arranged in a regular pattern;
    said abrasive field being situated at a distance of at least 0.2 mm from each of said apical edge and said coronal edge;
    said at least one longitudinal side being blank between said apical edge and said abrasive field, between said coronal edge and said abrasive field, between said first lateral end and said abrasive field and between said second lateral end and said abrasive field;
    wherein said abrasive field is configured for abrading and thus reducing the size of a tooth at a contact point between said abrasive field and the tooth when moving the strip in a linear motion.

2. The tool according to claim 1, wherein said distance is at most 2 mm.

3. The tool according to claim 1, wherein said abrasive field is rectangular.

4. The tool according to claim 1, wherein a blank portion of said at least one longitudinal side between said apical edge and said abrasive field is formed of a layer of titanium nitride or of a carbon layer.

5. The tool according to claim 1, wherein a blank portion of said at least one longitudinal side between said apical edge and said abrasive field is polished.

6. The tool according to claim 1, wherein a layer is applied to at least a portion of said support, wherein said abrasive particles are applied to at least one of said layer and said support in order to form said abrasive field.

7. The tool according to claim 1, wherein said at least one longitudinal side forms a first longitudinal side and said strip comprises a second longitudinal side opposite to said first longitudinal side, and wherein both of said longitudinal sides of said strip comprise a blank portion adjacent to said apical edge.

8. The tool according to claim 1, wherein said at least one longitudinal side forms a first longitudinal side, said apical edge forms a first apical edge and said abrasive field forms a first abrasive field, and wherein said strip comprises a second longitudinal side opposite to said first longitudinal side, said second longitudinal side comprising a second abrasive field arranged at a distance from a second apical edge of said second longitudinal side.

9. The tool according to claim 1, further comprising a bow for retaining said strip.

10. The tool according to claim 1, wherein said abrasive field is perforated.

11. A tool for treatment of interdental surfaces,
    said tool having a tool longitudinal axis and a first and second lateral end along said tool longitudinal axis;
    a strip comprising a support and including at least one longitudinal side; said strip extending from said first lateral end of said tool along said tool longitudinal axis to said second lateral end of said tool;
    said at least one longitudinal side of said strip comprising an apical edge extending along a first portion of said longitudinal axis, said apical edge being straight, and a coronal edge extending along a second portion of said longitudinal axis, said coronal edge also being straight;
    an abrasive field on at least one longitudinal side of said strip is provided with abrasive particles, which are arranged on said support, said support being flat so that it is free of geometrical protrusions arranged in a regular pattern;
    said abrasive field being arranged at a first distance from the apical edge and at a second distance from the coronal edge and being distanced away from the first lateral end and the second lateral end, the first distance being at least 0.2 mm and smaller than a height of said abrasive field;
    said at least one longitudinal side being blank between said apical edge and said abrasive field, and between said coronal edge and said abrasive field, and between said first lateral edge and said abrasive field and between said second lateral end and said abrasive field;
    wherein the abrasive field is configured for abrading and thus reducing the size of a tooth at a contact point between the abrasive field and the tooth when moving the strip in a linear motion.

12. The tool according to claim 11, wherein said first distance is at most 2 mm.

13. The tool according to claim 11, wherein said abrasive field is rectangular.

14. The tool according to claim 11, further comprising a bow for retaining said strip.

15. The tool according to claim 11, wherein said at least one longitudinal side forms a first longitudinal side and said strip further includes a second longitudinal side, opposite to said first longitudinal side, said second longitudinal side having another abrasive field, which is arranged at a distance from an apical edge of the second longitudinal side, wherein the second longitudinal side is blank between the apical edge of the second longitudinal side and its abrasive field.

16. A set of at least two tools according to claim 1, said tools differing with regard to at least one of the following parameters:
    the distance between the apical edge and the abrasive field, a grain size of abrasive particles forming the abrasive field.

* * * * *